United States Patent
Ano et al.

(10) Patent No.: US 9,131,699 B2
(45) Date of Patent: Sep. 15, 2015

(54) **METHOD FOR INHIBITING PROLIFERATION OF PLANT PATHOGENIC MICROBE USING *COLLIMONAS* BACTERIUM**

(75) Inventors: Takashi Ano, Kinokawa (JP); Yoichiro Hirose, Minato-ku (JP)

(73) Assignees: NEW ENVIRONMENTAL TECHNOLOGY COUNCIL, Chiyoda-ku, Tokyo (JP); KINKI UNIVERSITY, Higashiosaka-Shi, Osaka (JP)

( * ) Notice: Subject to any disclaimer, the term of this patent is extended or adjusted under 35 U.S.C. 154(b) by 0 days.

(21) Appl. No.: 14/344,365

(22) PCT Filed: Dec. 16, 2011

(86) PCT No.: PCT/JP2011/079246
§ 371 (c)(1),
(2), (4) Date: Mar. 12, 2014

(87) PCT Pub. No.: WO2013/038575
PCT Pub. Date: Mar. 21, 2013

(65) Prior Publication Data
US 2014/0348797 A1 Nov. 27, 2014

(30) Foreign Application Priority Data
Sep. 15, 2011 (WO) .................. PCT/JP2011/071097

(51) Int. Cl.
*A01N 63/00* (2006.01)
*C12N 1/20* (2006.01)
*C12R 1/01* (2006.01)

(52) U.S. Cl.
CPC *A01N 63/00* (2013.01); *C12N 1/20* (2013.01); *C12R 1/01* (2013.01)

(58) Field of Classification Search
IPC .................................... A01N 63/00; C12R 1/01
See application file for complete search history.

(56) References Cited

PUBLICATIONS

Mela, F. et al., "Dual transcriptional profiling of a bacterial/fungal confrontation: *Collimonas fungivorans* versus *Asperfillus niger*," *ISME J.* 5(9):1494-1504 (2011).
Uroz, S. et al., "Bacterial weathering and its contribution to nutrient cycling in temperate forest ecosystems," *Res. Microb.* 162(9):820-831 (2011).
Vu, B. et al., "Bacterial extracellular polysaccharides involved in biofilm," *Molecules* 14(7):2535-2554 (2009).
International Search Report (PCT/ISA/210) mailed on Apr. 3, 2012, by the Japanese Patent Office as the International Searching Authority for International Application No. PCT/JP2011/079246.
De Boer et al., "Anti-fungal properties of chitinolytic dune soil bacteria", Soil Biol. Biochem., Feb. 1998, pp. 193-203, vol. 30, No. 2.

(Continued)

*Primary Examiner* — Rosanne Kosson
(74) *Attorney, Agent, or Firm* — Buchanan Ingersoll & Rooney PC

(57) ABSTRACT

To provide a method for inhibiting the proliferation of a plant pathogenic bacterium. A method for inhibiting the proliferation of a plant pathogenic bacterium, including culturing a microorganism having an ability to inhibit the proliferation of a plant pathogenic bacterium and belonging to the genus *Collimonas*, and seeding the cultured microorganism to a plant soil.

5 Claims, 16 Drawing Sheets

(56) References Cited

PUBLICATIONS

De Boer et al., "*Collimonas fungivorans* gen. nov., sp. nov., a chitinolytic soil bacterium with the ability to grown on living fungal hyphae", International Journal of Systematic and Evolutionary Microbiology, May 2004, pp. 857-864, vol. 54.

Kamilova et al., "*Collimonas fungivorans*, an unpredicted in vitro but efficient in vivo biocontrol agent for the suppression of tomato foot and root rot", Environmental Microbiology, Jun. 2007, pp. 1597-1603, vol. 9, No. 6.

(a)

(b)

(c)

(d)

(a)

(b)

(c)

(a)

(b)

(c)

(a)

(b)

(c)

(a)

(b)

(c)

(a)

(b)

(c)

(a)

(b)

(c)

(a) (b)

(c) (d)

(a)

(b)

(c)

(a) 
(b) 
(c)

(d) 
(e)

(a)

(b)

(a) (b) (c)

(d) (e) (f)

(a) (b)

METHOD FOR INHIBITING PROLIFERATION OF PLANT PATHOGENIC MICROBE USING *COLLIMONAS* BACTERIUM

TECHNICAL FIELD

This invention relates to a method for inhibiting the proliferation of a plant pathogenic bacterium using a microorganism, and especially relates to a method for inhibiting the proliferation of a plant pathogenic bacterium using a *Collimonas* bacterium.

BACKGROUND ART

Conventionally, *Fusarium* bacteria as pathogenic bacteria of soil-borne diseases and *Rhizoctonia* bacteria represented by damping-off have been known.

In order to control these plant pathogenic bacteria, various agrochemicals having special chemical components have been considered and suggested, and other approaches different from chemical agrochemicals have been considered, and for example, studies for inhibiting the proliferation of plant pathogenic bacteria using *Collimonas* bacteria have been conducted (Non-Patent Literatures 1 to 4).

CITATION LIST

Patent Literature

Non-Patent Literature 1: Wieste de Boer, Johan H. J. Leveau, George A. Kowalchuk, Paulien J. A. Klein Gunnewiek, Edwin C. A. Abeln, Marian J. Figge, Klaas Sjollema, Jaap D. Janse and Johannes A. van Veen: *Collimonas fungivorans* gen. nov., sp. nov., a chitinolytic soil bacterium with the ability to grow on living fungal hyphae.

Non-Patent Literature 2: Francesca Mela, Kathrin Fritsche, Wietse de Boer, Johannes A van Veen, Leo H de Graaff, Marlies van den Berg and Johan H J Leveau: Dual transcriptional profiling of a bacterial/fungal confrontation: *Collimonas fungivorans* versus *Aspergillus niger*

Non-Patent Literature 3: Faina Kamilova, Johan H. J. Leveau and Ben Lugtenberg: *Collimonas fungivorans*, an unpredicted in vitro but efficient in vivo biocontrol agent for the suppression of tomato foot and root rot Non-Patent Literature 4: Sachie Hoppener-Ogawa: Ecology of mycrophagous *Collimonas* bacteria in soil Non-Patent Literature 5: Uroz, S., et al., Bacterial weathering and its contribution to nutrient cycling in temperate forest ecosystems, Research in Microbiology (2011)

Non-Patent Literature 6: Barbara Vu, Miao Chen, Russell J. Crawford and Elena P. Ivanova: Bacterial Extracellular Polysaccharides Involved in Biofilm.

Non-Patent Literature 7: Wieste de Boer, Johan H. J. leveau, George A. Kowalchuk, paulien J. A. Klein Gunnewiek, Edwin C. A. Abeln, Marian J. Figge, Klaas Sjollema, Jaap D. Janse and Johannes A. Van Veen: *Collimonas fungivorans* gen. nov., sp. nov., a chitinolytic soil bacterium with the ability to grow on living fungal hyphae.

Non-Patent Literature 8: Shiho Suzuki, "Physical and functional properties of novel polysaccharide films"

Non-Patent Literature 9: Francesca Meld, Kathrin Fritsche, Wietse de Boer, Johannes A van Veen, Leo H de Graaff, Marlies van den Berg and Johan H J Leveau: Dual transcriptional profiling of a bacterial/fungal confrontation: *Collimonas fungivorans* versus *Aspergillus niger*.

SUMMARY OF THE INVENTION

Technical Problem

*Collimonas* bacteria are known as microorganisms that proliferate in an oligotrophic environment, for example, microorganisms that proliferate in a $1/10$ TSB culture medium obtained by diluting a TSB culture medium to 10-fold, or a R2A culture medium, but are hard to proliferate in a culture medium containing much nutrient (Non-Patent Literature 5).

Furthermore, although *Collimonas* bacteria are known for their mycophagous action on plant pathogenic bacteria, this mycophagous action is expressed in the case when there is no nutrient source other than plant pathogenic bacteria, and it has not been confirmed that the mycophagous action is expressed in a culture medium containing an abundance of nutrient source.

Therefore, the present invention aims at providing a novel method for inhibiting the proliferation of a plant pathogenic bacterium by using a *Collimonas* bacterium.

Solution to Problem

In order to solve the above-mentioned problem, the inventors tried to conduct culturing under a condition that is different from a $1/10$ TSB culture medium and the like, by using a *Collimonas* bacterium, D-25 strain, which was deposited with the accession number NITE P-1104 with the Patent Microorganisms Depositary of the National Institute of Technology and Evaluation (2-5-8, Kazusakamatari, Kisarazu-shi, Chiba, Japan) (hereinafter referred to as "D-25 strain") on Jun. 9, 2011, and considered whether or not this strain is having an ability to inhibit the proliferation of plant pathogenic bacteria.

Consequently, they found that D-25 strain finely proliferates on a culture medium containing much nutrient and inhibits the proliferation of plant pathogenic bacteria *Rhizoctonia solani* and *Fusarium oxysporum* on a culture medium containing much nutrient, and attained the present invention.

Meanwhile, it has not been reported yet that a *Collimonas* bacterium clearly inhibits the proliferation of plant pathogenic bacteria *Rhizoctonia solani* and *Fusarium oxysporum* in either a conventional oligotrophic culture medium condition or a culture medium condition containing an abundance of nutrient source.

Specifically, the present invention is a method for inhibiting the proliferation of a plant pathogenic bacterium, including culturing a microorganism having an ability to inhibit the proliferation of a plant pathogenic bacterium and belonging to the genus *Collimonas*, and seeding the cultured microorganism to a plant soil.

The above-mentioned microorganism can effectively inhibit the proliferation of a plant pathogenic bacterium by being cultured on a culture medium in which culture medium components are not diluted, to form a biofilm.

Furthermore, the above-mentioned microorganism is a microorganism selected from D-25 strain, which was deposited with the accession number NITE P-1104, *Collimonas* NBRC3740 strain and *Collimonas fungivorans* DMZ17622 strain.

Furthermore, the plant pathogenic bacterium is a filamentous bacterium belonging to the genus *Rhizoctonia* or the genus *Fusarium*.

Advantageous Effects of Invention

According to the present invention, a novel method for inhibiting the proliferation of a plant pathogenic bacterium by using a *Collimonas* bacterium can be provided.

BRIEF DESCRIPTION OF DRAWINGS

FIGS. 3(a) to 3(d) are drawings showing the inhibition of the proliferation of plant pathogenic bacteria *Rhizoctonia solani* and *Fusarium oxysporum* by D-25 strain, in which FIG. 3(a): only *Rhizoctonia solani* was cultured on a TSA culture medium, FIG. 3(b): *Rhizoctonia solani* was seeded to a TSA culture medium on which D-25 strain had been cultured, FIG. 3(c): only *Fusarium oxysporum* was cultured on a TSA culture medium, and FIG. 3(d): *Fusarium oxysporum* was seeded to a TSA culture medium on which D-25 strain had been cultured.

FIGS. 4(a) to 4(c) are drawings showing the inhibition of the proliferation of a plant pathogenic bacterium. *Rhizoctonia solani* (*Rhizoctonia*) by D-25 strain that had been phagocytized from a R2A culture medium to a TSA culture medium, in which FIG. 4(a): only *Rhizoctonia solani* (*Rhizoctonia*) was cultured on a TSA culture medium, FIG. 4(b): D-25 strain that had been seeded to a TSA culture medium was cultured for one day, and *Rhizoctonia solani* was then seeded thereto, and FIG. 4(c): D-25 strain that had been seeded to a TSA culture medium was cultured for two days, and *Rhizoctonia solani* was then seeded thereto.

FIGS. 5(a) and 5(b) are drawings showing the inhibition of the proliferation of a plant pathogenic bacterium *Fusarium oxysporum* by D-25 strain that had been phagocytized from a R2A culture medium to a TSA culture medium, in which FIG. 5(a): only *Fusarium oxysporum* was cultured on a TSA culture medium, FIG. 5(b): D-25 strain was cultured on a TSA culture medium for one day, and *Fusarium oxysporum* was then seeded thereto, and FIG. 5(c): D-25 strain was cultured on a TSA culture medium for two days, and *Fusarium oxysporum* was then seeded thereto.

FIGS. 6(a) to 6(c) are drawings showing the inhibition of the proliferation of a plant pathogenic bacterium *Rhizoctonia solani* by D-25 strain in the case when a cycle of transferring D-25 strain from a R2A culture medium to a ISA culture medium was conducted twice, in which FIG. 6(a): only *Rhizoctonia solani* was cultured on a TSA culture medium, FIG. 6(b): *Rhizoctonia solani* was seeded to the TSA culture medium simultaneously with the second seeding of the D-25 strain to the TSA culture medium, and FIG. 6(c): D-25 strain was cultured for a day after the second seeding of the D-25 strain to the TSA culture medium, and *Rhizoctonia solani* was then seeded thereto.

FIGS. 7(a) to 7(c) are drawings showing the inhibition of the proliferation of a plant pathogenic bacterium *Fusarium oxysporum* by D-25 strain in the case when a cycle of transferring D-25 strain from a R2A culture medium to a TSA culture medium was conducted twice, in which FIG. 7(a): only *Fusarium oxysporum* was cultured on a TSA culture medium, FIG. 7(b): *Fusarium oxysporum* was seeded to the TSA culture medium simultaneously with the second seeding of the D-25 strain to the TSA culture medium, and FIG. 7(c): D-25 strain was cultured for a day after the second seeding of the D-25 strain to the TSA culture medium, and *Fusarium oxysporum* was then seeded thereto.

FIGS. 8(a) to 8(c) are drawings showing the inhibition of the proliferation of a plant pathogenic bacterium *Rhizoctonia solani* by D-25 strain in the case when a cycle of transferring D-25 strain from a R2A culture medium to a TSA culture medium was conducted four times, in which FIG. 8(a): only *Rhizoctonia solani* was cultured on a TSA culture medium, FIG. 8(b): *Rhizoctonia solani* was seeded to the TSA culture medium simultaneously with the fourth seeding of the D-25 strain to the TSA culture medium, and FIG. 8(c): D-25 strain was cultured for a day after the fourth seeding of the D-25 strain to the TSA culture medium, and *Rhizoctonia solani* was then seeded thereto.

FIGS. 9(a) to 9(c) are drawings showing the inhibition of the proliferation of a plant pathogenic bacterium *Fusarium oxysporum* by D-25 strain in the case when a cycle of transferring D-25 strain from a R2A culture medium to a TSA culture medium was conducted four times, in which FIG. 9(a): only *Fusarium oxysporum* was cultured on a TSA culture medium, FIG. 9(b): *Fusarium oxysporum* was seeded to the TSA culture medium simultaneously with the fourth seeding of the D-25 strain to the TSA culture medium, and FIG. 9(c): D-25 strain was cultured for a day after the fourth seeding of the D-25 strain to the TSA culture medium, and *Fusarium oxysporum* was then seeded thereto.

FIGS. 11(a) to 11(d) are drawings showing the inhibition of the onset of a disease caused by *Rhizoctonia solani* on seeds of *Solanum lycopersicum* and *Cucumis sativus* that had been immersed in a broth of D-25 strain, in which FIG. 11(a) is the result of the observation of *Solanum lycopersicum*, FIG. 11(b) is the result of the observation of *Cucumis sativus*, FIG. 11(c) is the result of the observation of *Solanum lycopersicum* in the case when the distance between the D-25 strain and *Rhizoctonia* solani was extended, and FIG. 11(d) is the result of the observation of *Cucumis sativus* in the same case.

FIGS. 12(a) to 12(f) are drawings showing the observation of the growth of *Cucumis sativus* by a 1/10 PDA culture medium (0.6%), in which FIG. 12(a) is the case when only a *Cucumis sativus* seed was seeded to a 1/10 PDA culture medium, FIG. 12(b) is a partially enlarged drawing of the same case, FIG. 12(c) is the case when *Cucumis sativus* and *Rhizoctonia solani* were seeded to a 1/10 PDA culture medium, FIG. 12(d) is a partially enlarged drawing of the same case, FIG. 12(e) is the case when *Cucumis sativus*, *Rhizoctonia solani* and D-25 strain were seeded to a 1/10 PDA culture medium, and FIG. 12(f) is a partially enlarged drawing of the same case.

DETAILED DESCRIPTION OF THE INVENTION

An exemplary embodiment of the present invention will be explained below with referring to the attached drawings.
(Proliferation Properties of D-25 Strain Under Different Culture Media Conditions)

The D-25 strain according to the present invention was cultured by using solid and liquid culture media. The culture media used were the following five kinds: a TSB culture medium and a 1/10 TSB culture medium formed by diluting a TSB culture medium. to 10 times, as liquid culture media, and a TSA culture medium and a 1/10 TSA culture medium in which the above-mentioned two kinds of liquid culture media were respectively solidified with agar, and a R2A culture medium, as solid culture media. The components of the above-mentioned culture media are as follows.

TSB culture medium (1 L)

| | |
|---|---|
| Polypeptone | 20 g |
| Glucose | 2.5 g |
| NaCl | 5 g |
| $K_2HPO_4$ | 2.5 g |

1/10 TSB culture medium (1 L)

| | |
|---|---|
| Polypeptone | 2 g |
| Glucose | 0.25 g |
| NaCl | 0.5 g |
| $K_2HPO_4$ | 0.25 g |

TSA culture medium
A TSB culture medium is solidified with 1.5% agar.
1/10 TSA culture medium
A 1/10 TSB culture medium is solidified with 1.5% agar.
R2A culture medium (1 L)

| | |
|---|---|
| Polypeptone | 0.5 g |
| Yeast extract | 0.5 g |
| Casamino acid | 0.5 g |
| Glucose | 0.5 g |
| Soluble starch | 0.5 g |
| Pyruvic acid Na | 0.3 g |
| $K_2HPO_4$ | 0.3 g |
| $MgSO_4$ | 0.05 g |
| Agar | 15 g |

As a result of the proliferation tests for the D-25 strain on the above-mentioned respective culture media, the proliferation of the D-25 strain was observed on a liquid culture medium, a 1/10 TSB culture medium, at 24° C. and 30° C.

Furthermore, the proliferation of the D-25 strain was observed at 24° C. and 30° C. also on the solid culture media: the R2A culture medium and 1/10 TSA culture medium.

However, the proliferation of the D-25 strain was not observed on the above-mentioned respective culture media at 37° C.

Figure 10:
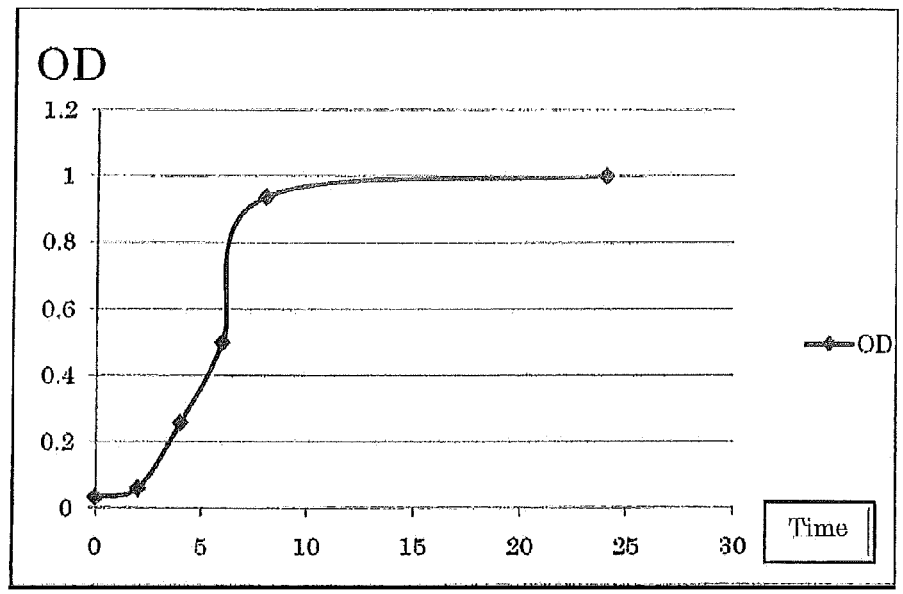
FIG. 10 is a proliferation curve of D-25 strain at 24° C. (2% seeded).

Furthermore, it was shown that several hours were required until the initiation of the proliferation was observed at 24° C., in the case of seeding of 1%, which is general as a seeding amount of the D-25 strain, whereas rapid proliferation was observed by increasing the seeding amount to 2% (FIG. 10). In addition, the number of bacteria was about $1.6 \times 10^8$ cfu/ml in a steady state.

Meanwhile, it is known that *Collimonas* bacteria are microorganisms that have a preference for oligotrophic states such as the above-mentioned 1/10 TSB culture medium and 1/10

TSA culture medium, and that the proliferation is not observed under a condition of abundant nutrients. Therefore, in order to verify these facts, confirmation experiments were conducted by using the above-mentioned TSA culture medium.

Figure 1:
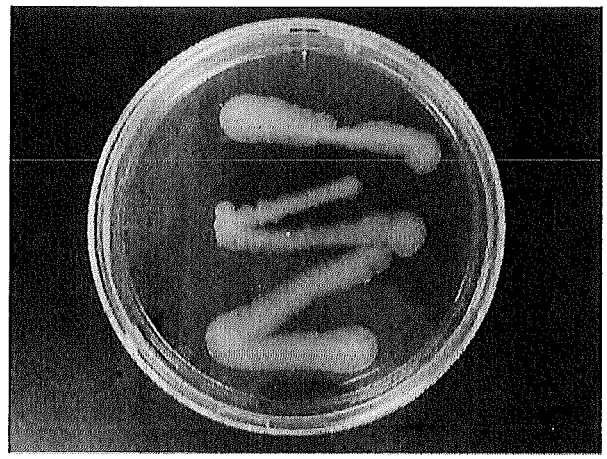
FIG. 1 is a drawing showing the proliferation of D-25 strain on a TSA culture medium (24° C.)

As a result, the proliferation of the D-25 strain was not observed or only very weak proliferation was partially observed on the TSA culture medium by culturing at 24° C. for a day. However, it was found that fine proliferation was shown on the $2^{nd}$ day (FIG. 1).

(Change in Number of Bacteria of *Collimonas* Bacterium in Sterilized Soil)

Secondly, an experiment for confirming the number of living bacteria of a *Collimonas* bacterium in a soil was conducted. Firstly, a *Collimonas* bacterium was cultured on a 1/10 TSB culture medium for 2 days under conditions of 24° C. and 200 rpm. Subsequently, 100 ml of a 1/10 TSB culture medium was added to a 500 ml flask, and the above-mentioned *Collimonas* bacterium was seeded thereto and cultured overnight at 24° C. and 200 rpm.

The above-mentioned cultured *Collimonas* bacterium was centrifuged by using a sterilized centrifugal tube, and the fungus body thereof was collected. The supernatant of the collected fungus body was removed, and the fungus body was suspended in 40 ml of sterilized water.

On the other hand, 10 g of a soil was put into a 100 ml beaker and sterilized, and the whole amount of the above-mentioned *Collimonas* bacteria suspended with sterilized water was added to this sterilized soil and mixed with a medicine spoon, and the change in the number of bacteria was measured. The sampling was conducted by collecting a little amount of the soil from five portions in the beaker, the weight was measured, the sample was then diluted to 10 times with sterilized water, a dilution series was then made, and the number of bacteria was calculated. The samples were collected on the first day, $2^{nd}$ day, $7^{th}$ day and $14^{th}$ day of the initiation of the experiment, and the respective numbers of bacteria of the *Collimonas* bacterium were calculated.

As a result, a number of bacteria of approximately $1.0^6$ cfu/g-soil was detected from the first day to the $14^{th}$ day, in terms of the number of bacteria per 1 g of the soil. As a result of three times of similar experiments, although there were errors of about double digits (100 times) in the measured values since the fungus body was not sufficiently collected due to the interaction of the soil particles and the fungus body of the *Collimonas* bacterium, the living of the fungus body seeded to the sterilized soil was observed.

Generally, it has been repeatedly reported that *Bacillus* bacteria, which are used in bioagrochemicals, have high auxotrophy and thus form spores under a soil environment containing poor nutrient source and become inactive in a dormant state, and thus the effects as agrochemicals are not stable.

On the other hand, with respect to the *Collimonas* bacterium, errors of about double digits (about 100 times) were observed among the experiments, whereas it was proved that the fungus body cultured in the flask had survivability of $10^6$ cfu/g-soil on average in the sterilized soil under an oligotrophic environment out of the flask.

Meanwhile, according to the previous experimental data and the like, it was reported that the growth number of a *Collimonas* bacterium in a soil was $10^5$ cfu/g-soil. Therefore, it can be judged that the experimental results at this time are almost data that is based on the biology of the *Collimonas* bacterium.

(Effect of Inhibiting Proliferation of Plant Pathogenic Bacterium by D-25 Strain)

An experiment for inhibiting the proliferation of a plant pathogenic bacterium *Rhizoctonia solani* was conducted by using D-25 strain, and the inhibition of the proliferation of the plant pathogenic bacterium *Rhizoctonia solani* was not observed at all in a R2A culture medium and a 1/10 TSA culture medium, or a PDA culture medium for a filamentous bacterium, and the like, and the D-25 strain was covered with the plant pathogenic bacterium *Rhizoctonia solani*.

Figure 2:
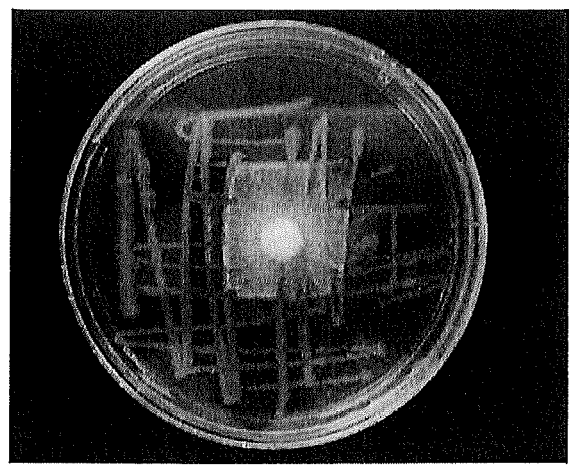
FIG. 2 is a drawing showing the effect of D-25 strain to inhibit the proliferation of a plant pathogenic bacterium *Rhizoctonia solani* on a TSA culture medium (24° C.).

Therefore, when the proliferation-inhibiting effect on the plant pathogenic bacterium *Rhizoctonia solani* at 24° C. was examined by using a TSA culture medium, as shown in FIG. 2, a phenomenon that the proliferation of the plant pathogenic bacterium *Rhizoctonia solani* seems to be blocked by the presence of the D-25 strain was observed.

Example 1

As mentioned above, the proliferation of D-25 strain was observed on a solid culture medium: TSA culture medium, in which culture medium components were not diluted, and a phenomenon that the proliferation of the plant pathogenic bacterium *Rhizoctonia solani* was blocked by the D-25 strain on the TSA culture medium was observed. Therefore, the reproducibility of the effect of D-25 strain to inhibit the proliferation of plant pathogenic bacteria *Rhizoctonia solani* and *Fusarium oxysporum* was attempted.

Experimental Method 1

(1) D-25 strain was seeded from a R2A culture medium to a TSA culture medium, and cultured at 24° C. for 2 days.
(2) A paper sheet on which lines had been drawn in a reticular pattern was attached to a petri dish, and D-25 strain was applied onto the above-mentioned TSA culture medium along the above-mentioned lines.
(3) Culturing was conducted at 24° C. overnight.
(4) A plant pathogenic bacterium: *Rhizoctonia solani* or *Fusarium oxysporum* was seeded to the center of the petri dish, and cultured at 24° C.
(5) As control culture media as criteria for comparison, TSA culture media onto which D-25 strain had not been applied, to which only a plant pathogenic bacterium *Rhizoctonia solani* or *Fusarium oxysporum* had been seeded, and which had been cultured at 24° C., were prepared, and these were compared with the above-mentioned TSA culture media onto which D-25 strain had been applied, to which the plant pathogenic bacterium *Rhizoctonia solani* or *Fusarium oxysporum* had been seeded.

Figure 3:
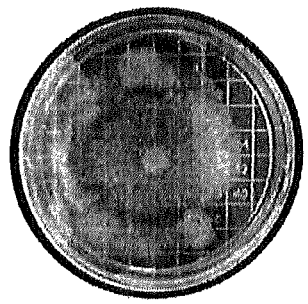
Figure 3:
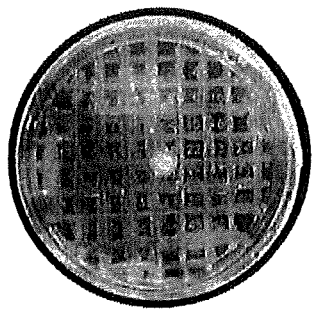
Figure 3:
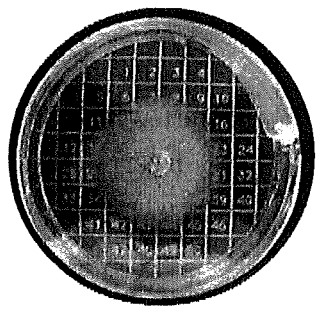
Figure 3:
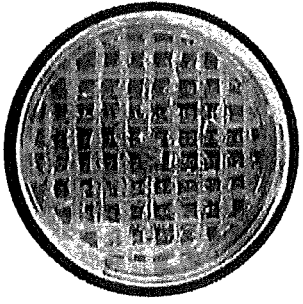

As a result thereof, as shown in FIGS. 3(*b*) and 3(*d*), it was shown that the proliferation of the plant pathogenic bacterium: *Rhizoctonia solani*, *Fusarium oxysporum* was completely inhibited by the D-25 strain cultured on the TSA culture medium, and thus the bacterium remained on the center of the petri dish.

On the other hand, in the petri dishes in which only the plant pathogenic bacterium *Rhizoctonia solani* or *Fusarium* oxysporum was cultured on the control culture medium, the above-mentioned two kinds of plant pathogenic bacteria showed fine proliferation within the same period (FIGS. 3(*a*) and 3(*c*)), and thus it was recognized also from this fact that the proliferation of the plant pathogenic bacterium *Rhizoctonia* solani or *Fusarium oxysporum* was inhibited by the D-25 strain cultured on the TSA culture medium, i.e., a culture medium in which culture medium components had not been diluted.

Experimental Method 2

(1) D-25 strain was seeded from a R2A culture medium to a TSA culture medium, and cultured at 24° C. for 1 day.

(2) D-25 strain was seeded from a R2A culture medium to a TSA culture medium, and cultured at 24° C. for 2 days.
(3) A paper sheet on which lines had been drawn in a square pattern was attached to a petri dish, and D-25 strain was applied onto each of the above-mentioned TSA culture media along the above-mentioned lines.
(4) The D-25 strain was further cultured for a predetermined period.
(5) Each of plant pathogenic bacteria *Rhizoctonia solani* or *Fusarium oxysporum* was seeded to the center of each of the petri dishes of the above-mentioned two kinds of TSA culture media, and cultured at 24° C. for 7 days.
(6) As control culture media as criteria for comparison, TSA culture media onto which D-25 strain had not been applied, to which only a plant pathogenic bacterium *Rhizoctonia solani* or *Fusarium oxysporum* had been seeded, which had been cultured at 24° C. for 7 days, were prepared, and these were compared with the TSA culture media onto which the D-25 strain had been applied, to which the plant pathogenic bacterium *Rhizoctonia solani* or *Fusarium oxysporum* had been seeded.

Figure 4:
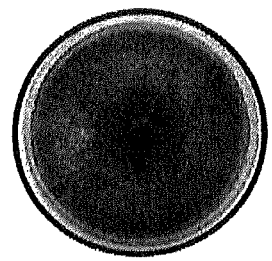
Figure 4:
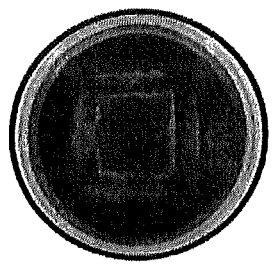
Figure 4:
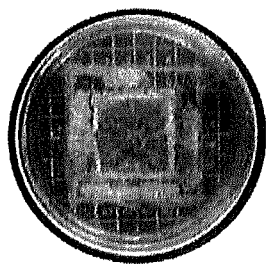
Figure 5:
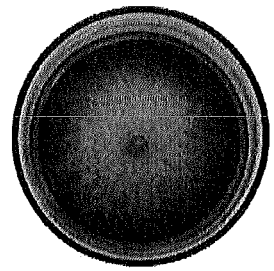
Figure 5:
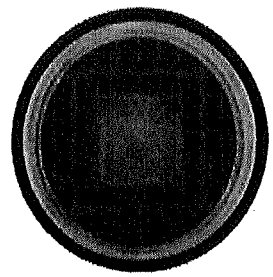
Figure 5:
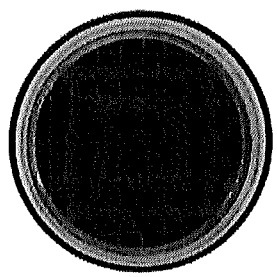
Figure 6:
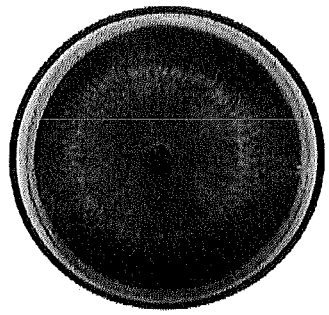
Figure 6:
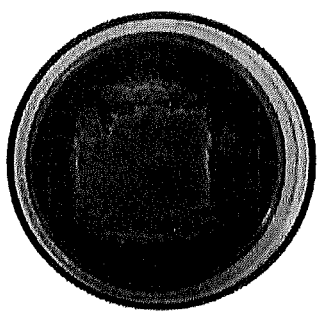
Figure 6:
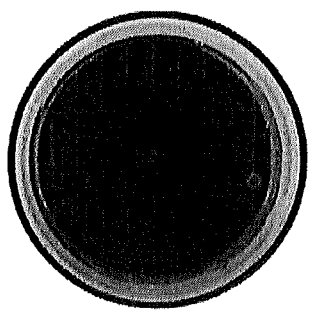
Figure 7:
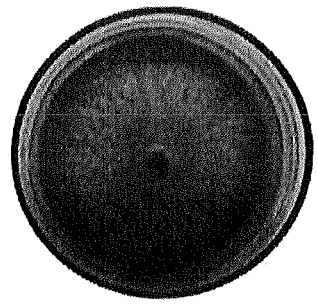
Figure 7:
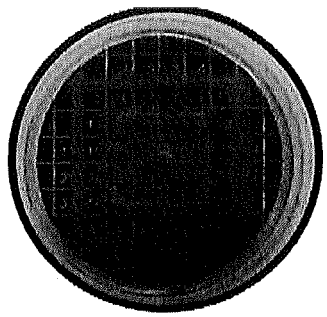
Figure 7:
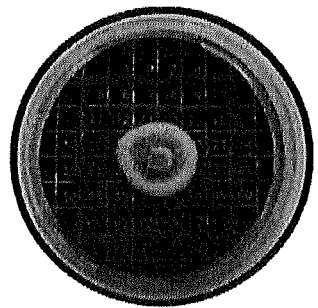
Figure 8:
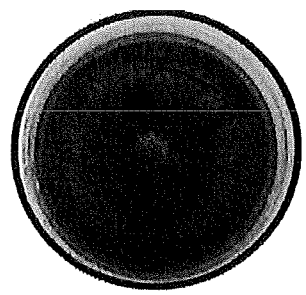
Figure 8:
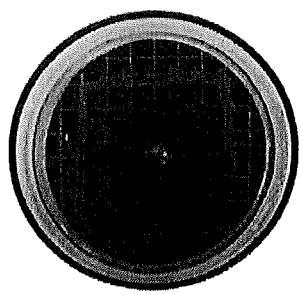
Figure 8:
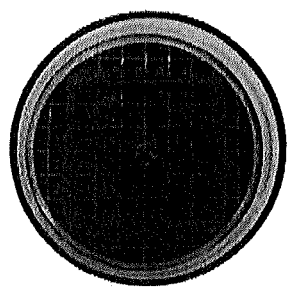
Figure 9:
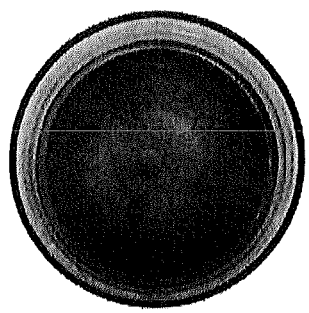
Figure 9:
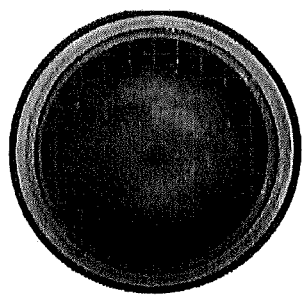
Figure 9:
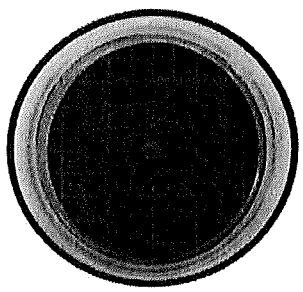

As shown in FIG. 4(b) and FIG. 5(b), it was recognized that the proliferation of the plant pathogenic bacteria *Rhizoctonia solani* and *Fusarium oxysporum* was inhibited by the D-25 strain despite that the seeding amount of the D-25 strain was decreased from the reticular pattern in FIG. 3 to the square shape.

Furthermore, as shown in FIG. 4(c) and FIG. 5(c), it was also shown that the ability of inhibiting the proliferation of the plant pathogenic bacteria *Rhizoctonia solani* and *Fusarium* oxysporum was higher at after 2 days when the D-25 strain had sufficiently proliferated.

Example 2

It is known that *Collimonas* bacteria proliferate on only oligotrophic culture media such as a ⅒ TSB culture medium and a ⅒ TSA culture medium. Therefore, it is considered that there is a possibility that a certain change (mutation) is caused by the proliferation of D-25 strain on general nutrient culture media found as mentioned above.

Therefore, D-25 strain is seeded from a R2A culture medium, which is an oligotrophic culture medium, to an enriched culture medium, a TSA culture medium, and proliferated, and the proliferated D-25 strain is seeded again to a R2A culture medium and proliferated. Thereafter the above-mentioned D-25 strain that had been proliferated on the R2A culture medium was seeded again to a TSA culture medium, and the ability of inhibiting the proliferation of plant pathogenic bacteria *Rhizoctonia* solani and *Fusarium oxysporum* was examined by using the D-25 strain that had been proliferated on the TSA culture medium.

In the present Example, culture media on which a cycle of transferring from a R2A culture medium to TSA culture medium had been conducted twice (from a R2A culture medium to a TSA culture medium, from the TSA culture medium to a R2A culture medium, and from the R2A culture medium to a TSA culture medium), and to which a plant pathogenic bacterium *Rhizoctonia solani* or *Fusarium* oxysporum had been simultaneously seeded, were respectively prepared. Furthermore, culture media obtained by culturing D-25 strain on a TSA culture medium for which the above-mentioned cycle had been conducted twice, and subsequently seeding thereto a plant pathogenic bacterium *Rhizoctonia solani* or *Fusarium* oxysporum, were respectively prepared. Meanwhile, the control culture medium as a criterion for comparison was identical with that of the above-mentioned Example, and thus the explanation thereof is omitted.

As shown in FIGS. 6(b) and 6(c), and FIGS. 7(b) and 7(c), an effect of inhibiting the proliferation of the plant pathogenic bacteria *Rhizoctonia solani* and *Fusarium* oxysporum was observed in both of the culture media to which the D-25 strain and the plant pathogenic bacterium *Rhizoctonia solani* or *Fusarium oxysporum* had been simultaneously seeded, and the culture media after the culturing of the D-25 strain for one day. Therefore, it was observed that the ability of inhibiting the proliferation of plant pathogenic bacteria had not been modified even after going through the TSA culture medium in which the culture medium components had not been diluted.

As mentioned above, it was shown that the ability of inhibiting the proliferation of plant pathogenic bacteria was not changed even after the D-25 strain went through the TSA culture medium in which the culture medium components had not been diluted. However, in order to confirm that the ability of inhibiting the proliferation of plant pathogenic bacteria is not changed even when the number of frequency of the transfer of culture media is increased, an observation was attempted by further increasing the cycles of transferring D-25 strain from a R2A culture medium to a TSA culture medium.

Culture media formed by changing the cycles of transferring D-25 strain from a R2A culture medium to a TSA culture medium from twice mentioned above to four times, and simultaneously seeding thereto a plant pathogenic bacterium *Rhizoctonia solani* or *Fusarium oxysporum*, were respectively prepared. Furthermore, culture media formed by conducting the above-mentioned cycles four times, thereafter culturing the D-25 strain on the TSA culture medium, and then seeding thereto a plant pathogenic bacterium *Rhizoctonia solani* or *Fusarium oxysporum*, were respectively prepared. Meanwhile, the control culture medium as a criterion for comparison was identical with that of the above-mentioned Example, and thus the explanation thereof is omitted.

As shown in FIGS. 8(b) and 8(c) and FIGS. 9(b) and 9(c), even when the cycles of transferring the D-25 strain from the R2A culture medium as an oligotrophic culture medium to the TSA culture medium as an enriched culture medium was increased to four times, no change was observed in the ability of the D-25 strain to inhibit the proliferation of the plant pathogenic bacteria. It was shown by this fact that the properties of the bacteria are not affected even when D-25 strain is proliferated in a large amount on a TSA culture medium.

Example 3

Secondly, some experiments were conducted so as to confirm whether or not the proliferation of a plant pathogenic bacterium can be inhibited by using the D-25 strain for plants.

The D-25 strain was cultured on 2 ml of a ⅒ TSB culture medium for 2 days at 24° C. and 200 rpm. Seed sterilization was then conducted to thereby allow the pre-germination of seeds of *Solanum lycopersicum* and *Cucumis sativus* on an agar culture medium (Agar 2%), and each seed was immersed in a broth of the above-mentioned D-25 strain and seeded to a PDA culture medium. Furthermore, seeds of *Solanum lycopersicum* and *Cucumis sativus* that had not been immersed in the above-mentioned broth were each seeded as a control to the above-mentioned PDA culture medium. After the seeding of the above-mentioned seeds, a plant pathogenic bacterium *Rhizoctonia solani* was seeded to the centers of the above-mentioned PDA culture media, and the onset of a disease on the seeds that had been immersed in the above-mentioned broth and the seeds that had not been immersed was observed.

Figure 11:
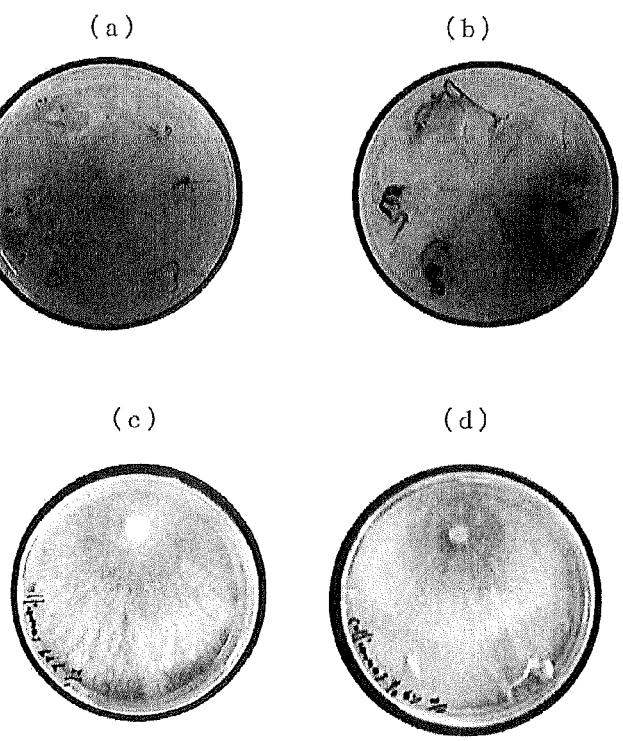

As shown in FIGS. 11(*a*) and 11(*b*), both of the seeds that had been immersed in the above-mentioned broth (the three seeds in the left of FIGS. 11(*a*) and 11(*b*)) and the seeds that had not been immersed (the three seeds in the right of FIGS. 11(*a*) and 11(*b*)) were infected with the plant pathogenic bacterium *Rhizoctonia solani*, and thus the inhibition of the proliferation of the plant pathogenic bacterium by the D-25 was not observed.

In the above-mentioned experiment, since the plant pathogenic bacterium *Rhizoctonia solani* was put on the center of the PDA culture medium, it was considered that the distance with the D-25 strain was short. Therefore, an experiment for extending the distance between the D-25 strain and the plant pathogenic bacterium *Rhizoctonia solani* was conducted, but the result was such that the inhibition of the proliferation of the plant pathogenic bacterium was not observed as shown in FIGS. 11(*c*) and 11(*d*).

Example 4

The D-25 strain was cultured on 2 ml of a 1/10 TSB culture medium for 2 days at 200 rpm and 24° C. 100 ml of 1/10 TSB was added to a 500 ml flask, and 2% of the above-mentioned D-25 strain was seeded thereto and cultured at 120 rpm. After the culturing, the above-mentioned D-25 strain was collected by centrifugation and re-suspended in 1 ml of sterilized distilled water.

35 ml of a 1/10 PDA culture medium (Agar 0.6%) was added to a test tube, and 0.1 ml of the above-mentioned suspension liquid of D-25 strain was seeded to the above-mentioned 1/10 PDA culture medium, together with a *Cucumis sativus* seed that had been subjected to seed sterilization and then put to pre-germination. A plant pathogenic bacterium *Rhizoctonia solani* was seeded to this culture medium, and the onset of a disease on the seed was observed.

As the criteria for comparison, a culture medium obtained by seeding a *Cucumis sativus* seed that had been subjected to seed sterilization and then put to pre-germination to the above-mentioned 1/10 PDA culture medium (Control 4-1), and a culture medium obtained by seeding a *Cucumis sativus* seed that had been subjected to seed sterilization and then put to pre-germination and a plant pathogenic bacterium *Rhizoctonia solani* to the above-mentioned 1/10 PDA culture medium (Control 4-2) were prepared.

Figure 12:
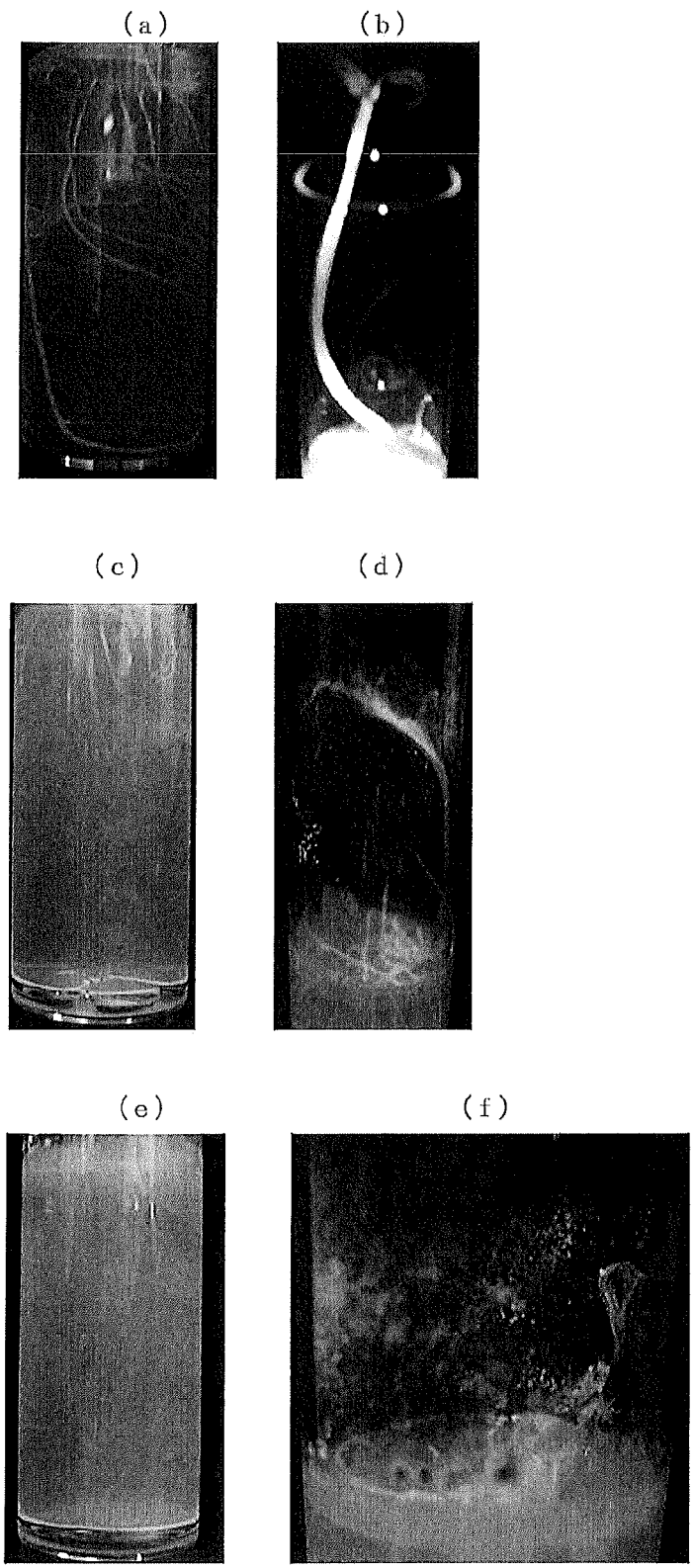

As shown in FIG. 12, the *Cucumis sativus* seed grew with no special problem in Control 4-1 (FIGS. 12(*a*) and 12(*b*)), whereas in Control 4-2, the *Cucumis sativus* seed was infected with the plant pathogenic bacterium *Rhizoctonia solani*, the stem turned into brown, and the root died of infection with mycelia (FIGS. 12(*c*) and 12(*d*)).

Furthermore, as shown in FIGS. 12(*e*) and 12(*f*), also in the case when 0.1 ml of the above-mentioned suspension liquid of D-25 strain was seeded, the *Cucumis sativus* seed was infected with the plant pathogenic bacterium *Rhizoctonia solani*, and the stem and root did not grow but turned into brown and died.

Example 5

In this Example, a TSB culture medium was used as a liquid culture medium. The D-25 strain was cultured on a TSB culture medium, a 500 ml flask to which 100 ml of TSB had been added was prepared, and the above-mentioned D-25 strain was seeded thereto and cultured. After the culturing, the above-mentioned D-25 strain was collected by centrifugation and re-suspended with 40 ml of sterilized distilled water. 10 ml of a suspension liquid of this D-25 strain was added to a test tube to which a 1/10 PDA culture medium had been injected, the following test specimens were prepared, and the abilities of inhibiting the proliferation of a plant pathogenic bacterium *Rhizoctonia solani* were observed.

Test Specimen 5-1

A test specimen obtained by seeding the D-25 strain that had been cultured on a TSB culture medium to a 1/10 PDA culture medium, and seeding thereto a plant pathogenic bacterium *Rhizoctonia solani*, and a *Cucumis sativus* seed that had been subjected to seed sterilization and then put to pre-germination.

Test Specimen 5-2

A test specimen obtained by seeding the D-25 strain that had been cultured on a TSB culture medium to a 1/10 PDA culture medium, seeding thereto a plant pathogenic bacterium *Rhizoctonia solani*, a *Cucumis sativus* seed that had been subjected to seed sterilization and then put to pre-germination, and dropping 200 µl of a concentrated liquid of the above-mentioned D-25 strain thereto.

Test Specimen 5-3

A test specimen obtained by seeding the D-25 strain that had been cultured on a TSB culture medium to a 1/10 PDA culture medium, seeding thereto a *Cucumis sativus* seed that had been immersed in a broth of the above-mentioned D-25 and a plant pathogenic bacterium *Rhizoctonia solani*, and dropping 200 µl of a concentrated liquid of the above-mentioned D-25 strain thereto.

Figure 13:
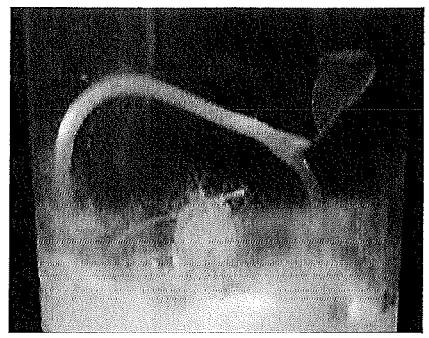
FIG. 13(a) shows an observation drawing of *Cucumis sativus* in the case when *Rhizoctonia solani* and a *Cucumis sativus* seed were seeded to a 1/10 PDA culture medium on which D-25 strain cultured on a TSB culture medium had been seeded.
FIG. 13(b) shows an observation drawing of *Cucumis sativus* in the case when *Rhizoctonia solani* and a *Cucumis sativus* seed were seeded to a 1/10 PDA culture medium on which D-25 strain cultured on a TSB culture medium had been seeded, and 200 µl of a concentrated liquid of D-25 strain was added thereto.
FIG. 13(c) shows an observation drawing of *Cucumis sativus* in the case when a *Cucumis sativus* seed that had been immersed in a broth of D-25 strain, and *Rhizoctonia solani* were seeded to a 1/10 PDA culture medium on which D-25 strain cultured on a TSB culture medium had been seeded, and 200 µl of a concentrated liquid of D-25 strain was added thereto.
Figure 13:
Figure 13:

With respect to the *Cucumis sativus* seed in Test Specimen 5-1, the growth thereof was not so good, but a phenomenon that the stem did not die and the disease progressed more slowly as compared to the *Cucumis sativus* seed in Control 4-2 of Example 4 was observed (FIG. 13(*a*)).

With respect to the *Cucumis sativus* seed in Test Specimen 5-2, the seed was infected with the plant pathogenic bacterium *Rhizoctonia solani* as in Test Specimen 5-1, even though the concentrated liquid of the above-mentioned D-25 strain was dropped onto the 1/PDA culture medium (FIG. 13(*b*)).

With respect to the *Cucumis sativus* seed in Test Specimen 5-3, the seed was infected with the plant pathogenic bacterium *Rhizoctonia solani* as in Test Specimen 5-1, even though the seed was immersed in the broth of the D-25 strain (FIG. 13(*c*)).

It is presumed from the above-mentioned Examples 3 to 5 that, when a liquid is present on the surface of an agar culture medium, the mycelia of a plant pathogenic bacterium *Rhizoctonia solani* extend before the ability of D-25 strain to inhibit the plant pathogenic bacterium is exerted, and thus infection to a plant seed easily progresses.

Therefore, it was proved that it is necessary to seed D-25 strain, which has stickiness as observed on a TSA culture medium, in a state in which a free liquid is present as little as possible, in the suppression of a plant pathogenic bacterium by the D-25 strain.

Example 6

In this Example, the culture medium for culturing D-25 strain was changed from a liquid culture medium to a solid culture medium, a TSA culture medium. The D-25 strain that had been cultured on the TSA culture medium was collected by using a spatula, the following test specimens were prepared, and the abilities of inhibiting the proliferation of a plant pathogenic bacterium *Rhizoctonia solani* were observed.

Test Specimen 6-1

A test specimen obtained by putting a 1/10 PDA culture medium (Agar 0.6%) into Agripot, and seeding a *Cucumis sativus* seed that had been subjected to seed sterilization and then put to pre-germination to the above-mentioned 1/10 PDA culture medium.

Test Specimen 6-2

A test specimen obtained by putting a 1/10 PDA culture medium (Agar 0.6%) into Agripot, and seeding a *Cucumis sativus* seed that had been subjected to seed sterilization and then put to pre-germination and a plant pathogenic bacterium *Rhizoctonia* solani to the above-mentioned 1/10 PDA culture medium.

Test Specimen 6-3

A test specimen obtained by putting a 1/10 FDA culture medium (Agar 0.6%) into Agripot, and seeding a *Cucumis sativus* seed that had been subjected to seed sterilization and then put to pre-germination and D-25 strain that had been cultured on a TSA culture medium (in an amount corresponding to a piece of TSA) to the above-mentioned 1/10 FDA culture medium.

Test Specimen 6-4

A test specimen obtained by putting a 1/10 PDA culture medium (Agar 0.6%) into Agripot, and seeding a *Cucumis sativus* seed that had been subjected to seed sterilization and then put to pre-germination, D-25 strain that had been cultured on a TSA culture medium (in an amount corresponding to a piece of TSA) and a plant pathogenic bacterium *Rhizoctonia solani* to the above-mentioned 1/10 PDA culture medium.

Test Specimen 6-5

A test specimen obtained by putting a 1/10 PDA culture medium (Agar 0.6%) into Agripot, and seeding a *Cucumis sativus* seed that had been subjected to seed sterilization and then put to pre-germination, D-25 strain that had been cultured on a TSA culture medium (in an amount corresponding to three pieces of TSA) and a plant pathogenic bacterium *Rhizoctonia solani* to the above-mentioned 1/10 PDA culture medium.

Figure 14:
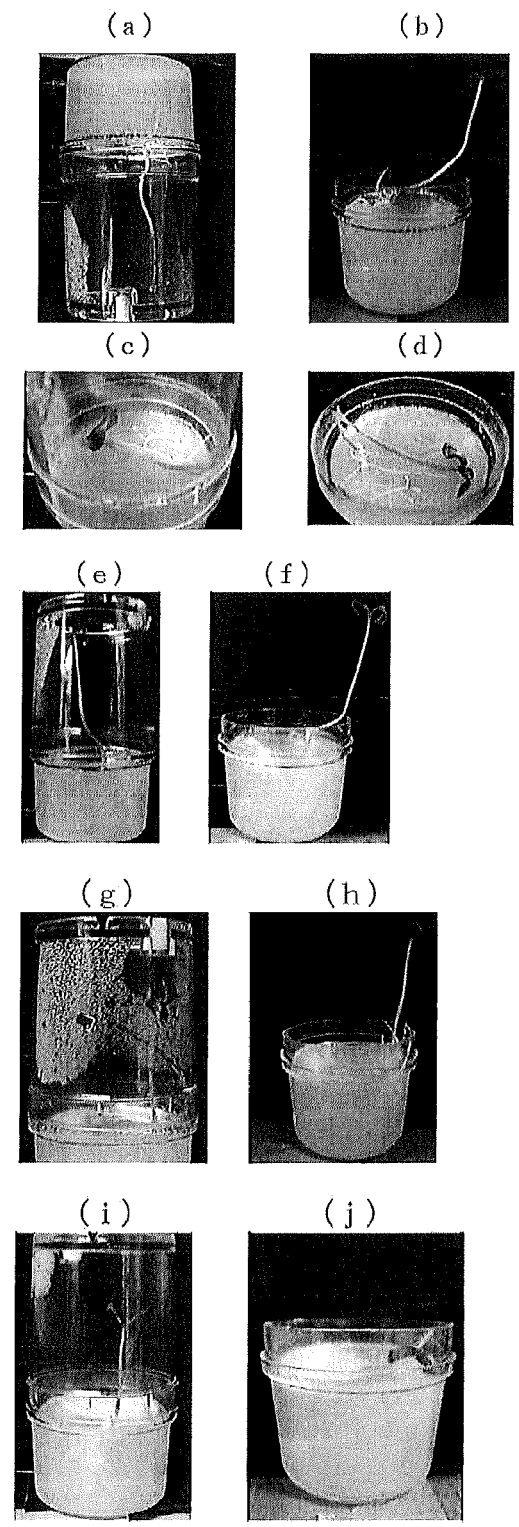
FIG. 14 (*a*) is an observation drawing on the 5$^{th}$ day after seeding of a *Cucumis sativus* seed to a 1/10 PDA culture medium, FIG. 14 (*b*) is an observation drawing on the 7$^{th}$ day in the same case, FIG. 14 (*c*) is an observation drawing on the 5$^{th}$ day after seeding of a *Cucumis sativus* seed and *Rhizoctonia solani* to a 1/10 PDA culture medium, FIG. 14(*d*) is an observation drawing on the 7$^{th}$ day in the same case, FIG. 14(*e*) is an observation drawing on the 5$^{th}$ day after seeding of a *Cucumis sativus* seed and D-25 strain (in an amount corresponding to a piece of TSA) to a 1/10 PDA culture medium, FIG. 14 (*f*) is an observation drawing on the 7$^{th}$ day in the same case, FIG. 14(*g*) is an observation drawing on the 5$^{th}$ day after seeding of a *Cucumis sativus* seed, D-25 strain (in an amount corresponding to a piece of TSA) and *Rhizoctonia solani* to a 1/10 PDA culture medium, FIG. 14 (*h*) is an observation drawing on the 7$^{th}$ day in the same case, FIG. 14(*i*) is an observation drawing on the 5$^{th}$ day after seeding of a *Cucumis sativus* seed, D-25 strain (in an amount corresponding to three pieces of TSA) and *Rhizoctonia solani* to a 1/10 PDA culture medium, and FIG. 14(*j*) is an observation drawing on the 7$^{th}$ day in the same case.

As shown in FIG. 14, it was shown that the time until the infection with the plant pathogenic bacterium can be extended by a colony of D-25 strain having stickiness, which is collected on a TSA culture medium, and it was expected that the effect of inhibiting the proliferation of the plant pathogenic bacterium becomes more significant by devising the method for seeding the above-mentioned D-25 strain having stickiness.

Therefore, the following test specimens of D-25 strain were further prepared, and the ability of inhibiting the proliferation of the plant pathogenic bacterium *Rhizoctonia solani* was observed.

Test Specimen 6-6

A test specimen obtained by putting a 1/10 PDA culture medium (Agar 0.6%) into Agripot, and seeding thereto a *Cucumis sativus* seed that had been subjected to seed sterilization and put to pre-germination.

Test Specimen 6-7

A test specimen obtained by putting a 1/10 PDA culture medium (Agar 0.6%) into Agripot, and sending thereto a *Cucumis sativus* seed that had been subjected to seed sterilization and put to pre-germination and a plant pathogenic bacterium *Rhizoctonia*

Test Specimen 6-8

A test specimen obtained by putting a 1/10 PDA culture medium (Agar 0.6%) into Agripot, applying D-25 strain that had been cultured on a TSA culture medium (in an amount corresponding to two pieces of TSA) onto the entirety of the culture medium, and seeding thereto a *Cucumis sativus* seed that had been subjected to seed sterilization and put to pre-germination.

Test Specimen 6-9

A test specimen obtained by putting a 1/10 PDA culture medium (Agar 0.6%) into Agripot, applying D-25 strain that has been cultured on a TSA culture medium (in an amount corresponding to two pieces of TSA) onto the entirety of the culture medium, and seeding a *Cucumis sativus* seed that had been subjected to seed sterilization and put to pre-germination and a plant pathogenic bacterium *Rhizoctonia solani*.

Test Specimen 6-10

A test specimen obtained by putting a 1/10 PDA culture medium (Agar 0.6%) into Agripot, applying D-25 strain that has been cultured on a TSA culture medium (in an amount corresponding to a piece of TSA) onto the entirety of the culture medium, and seeding thereto a *Cucumis sativus* seed that had been subjected to seed sterilization and put to pre-germination and a plant pathogenic bacterium *Rhizoctonia solani*.

Figure 15:
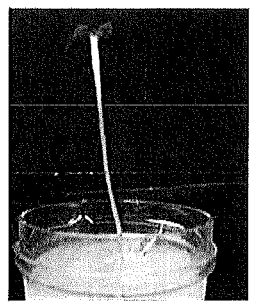
FIG. 15(*a*) is an observation drawing in the case when a *Cucumis sativus* seed was seeded to a 1/10 PDA culture medium, FIG. 15 (*b*) is an observation drawing in the case when a *Cucumis sativus* seed and *Rhizoctonia solani* were seeded to a 1/10 PDA culture medium, FIG. 15 (*c*) is an observation drawing in the case when a *Cucumis sativus* seed and D-25 strain (in an amount corresponding to two pieces of TSA) were seeded La a 1/10 PDA culture medium, FIG. 15 (*d*) is an observation drawing in the case when a *Cucumis sativus* seed, D-25 strain (in an amount corresponding to two pieces of TSA) and *Rhizoctonia solani* were seeded to a 1/10 PDA culture medium, and FIG. 15(*e*) is an observation drawing in the case when a *Cucumis sativus* seed, D-25 strain (in an amount corresponding to a piece of TSA) and *Rhizoctonia solani* were seeded to a 1/10 PDA culture medium.
Figure 15:
Figure 15:
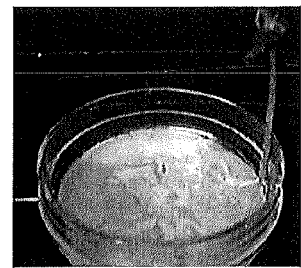
Figure 15:
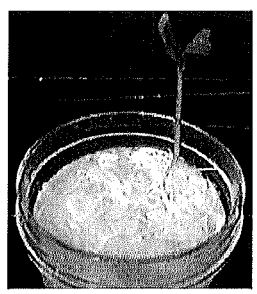
Figure 15:
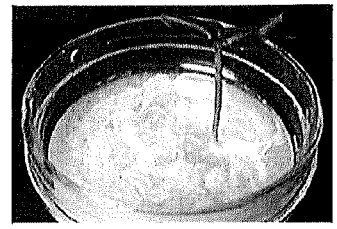

As shown in FIGS. 15(*c*), 15(*d*) and 15(*e*), the infection of the plant pathogenic bacterium to the *Cucumis sativus* seed was prevented from the initiation of the experiment to the $7^{th}$ day, despite a culture medium that is advantageous to the proliferation of the plant pathogenic bacterium *Rhizoctonia solani* and an experimental environment that is advantageous to small and closed infection as in the present Example.

It was shown by these serial results that the ability of D-25 strain to inhibit the proliferation of the plant pathogenic bacterium is significant in the case when a slime-like colony having stickiness is formed by culturing on a solid culture medium such as a TSA culture medium.

A colony cultured by such means is generally called as "biofilm", and is a colony of bacteria in the natural world constituted by mainly extracellular polysaccharides, and as is known by Non-Patent Literature 6, the existence of an expression system of a gene that is different from those of planktonic cells by aerated and agitated culturing that is generally used in bioagrochemicals is suggested. It was shown by the experimental result at this time that a biofilm composition of the bacterium by solid culturing or other culturing means is effective for inhibiting the proliferation of a plant pathogenic bacterium by D-25 strain.

Example 7

In order to confirm whether or not a substance that inhibits the proliferation of a plant pathogenic bacterium *Rhizoctonia solani* is produced from D-25 strain, an experiment for inhibiting the proliferation (of *Rhizoctonia solani*) was conducted by using a supernatant of D-25 strain.

D-25 strain was cultured on 2 ml of a 1/10 TSB culture medium for 2 days. Thereafter 100 ml of a 1/10 TSB culture medium was added to a 500 ml flask, and 2% of the above-mentioned D-25 strain was seeded thereto and cultured at 24° C. and 120 rpm for 5 days. The above-mentioned cultured D-25 strain was centrifuged at 15,000 rpm, and sterilization with a 0.2 μm (ADVANTEC) filter was conducted to give a supernatant of D-25 strain.

The TSA culture medium was added by 9, 7 and 5 ml, respectively, to 1, 3 and 5 ml of the supernatant obtained above so that the total amount became 10 ml. As controls, 1, 3 and 5 ml of a 1/10 TSA culture medium were prepared instead of the supernatant, and the ability of inhibiting the proliferation of a plant pathogenic bacterium *Rhizoctonia solani* was examined on each specimen.

Figure 16:
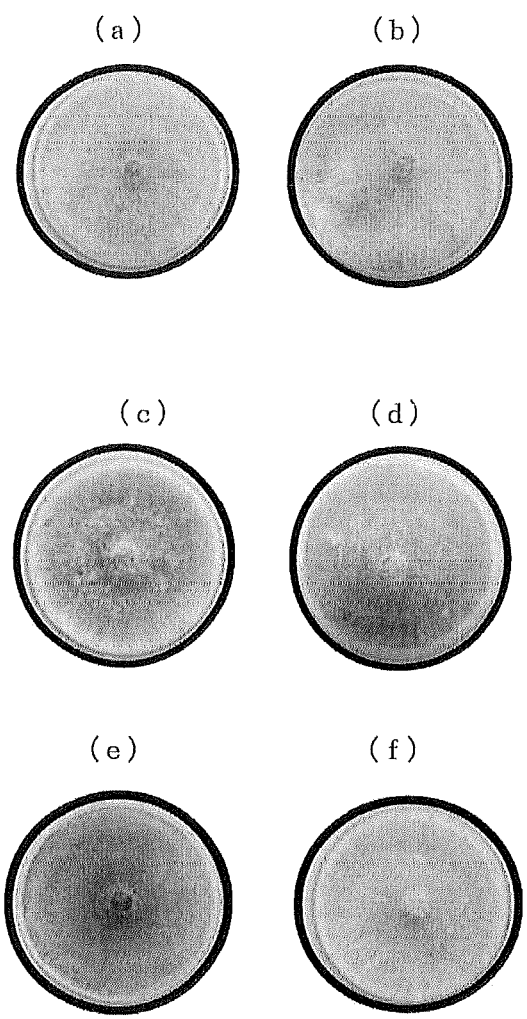
FIGS. 16(*a*) to 16(*f*) are observation drawings of the inhibition of the proliferation of *Rhizoctonia solani* by a supernatant of a broth of D-25 strain, in which FIG. 16(*a*): 1 ml of a 1/10 TSA culture medium as a control, FIG. 16(*b*): the case when the supernatant was 1 ml, FIG. 16(*c*): 3 ml of a 1/10 TSA culture medium as a control, FIG. 16(*d*): the case when the supernatant was 3 ml, FIG. 16(*e*): 5 ml of a 1/10 TSA culture medium as a control, and FIG. 16(*f*): the case when the supernatant was 5 ml.

As shown in FIG. 16(f), even when 5 ml of the supernatant of broth of D-25 strain was used, the ability of inhibiting the proliferation of the plant pathogenic bacterium was not observed, and thus it was judged that an antibacterial active substance that inhibits the proliferation of the plant pathogenic bacterium *Rhizoctonia solani* was not produced by D-25 strain. Namely, D-25 strain can inhibit the proliferation of the plant pathogenic bacterium *Rhizoctonia solani* without depending on an antibiotic substance that is generated by a bacterium, which is generally used in bioagrochemicals.

Example 8

In the present Example, an experiment for inhibiting the proliferation of a plant pathogenic bacterium *Rhizoctonia solani* was conducted by using a *Collimonas* bacterium other than the D-25 strain. The *Collimonas* bacterium used was NBRC3740 strain (former name: *Janthinobacterium lividum*) and the ability of inhibiting the proliferation of the plant pathogenic bacterium was compared with that of D-25 strain by using NBRC3740 strain that had been proliferated on an agar culture medium in a liquid-cultured NBRC3740 strain.

D-25 strain was cultured by using a TSA culture medium, and NBRC3740 strain was proliferated by using a multiple water culture medium, the respective fungus bodies were collected, and the abilities of inhibiting the proliferation of the plant pathogenic bacterium were compared. Since it was concerned that the number of bacteria of NBRC3740 strain was small, the NBRC3740 strain was applied onto 15 pieces of multiple water culture media and collected by using a spatula. The collected bacteria were each applied onto a petri dish, and the plant pathogenic bacterium *Rhizoctonia solani* was seeded to the center and cultured at 24° C. for 3 days.

Figure 17:
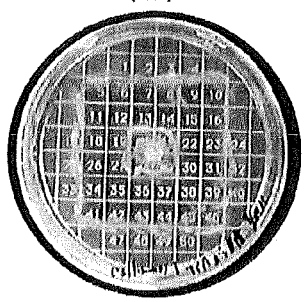
FIG. 17(*a*) is an observation drawing of the inhibition of the proliferation of *Rhizoctonia solani* by D-25 strain, and FIG. 17(*b*) is an observation drawing of the inhibition of the proliferation of *Rhizoctonia solani* by NBRC3740 strain.
Figure 17:
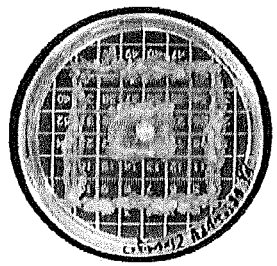

As shown in FIG. 17(a), D-25 strain inhibited the proliferation of the plant pathogenic bacterium *Rhizoctonia* solani, whereas the mycelia of NBRC3740 strain proliferated to the outer wall. The fungus body in an amount corresponding to a piece of a TSA culture medium was used for D-25 strain, and the fungus body in an amount corresponding to 15 pieces of condensed water culture media was used for NBRC3740 strain, and as is also apparent from FIG. 17(b), the fungus body of NBRC3740 strain was used in a sufficiently larger amount than that of the fungus body of D-25 strain. However, significant inhibition was not observed as compared to D-25 strain.

It was judged from the above-mentioned result of the use of the liquid-cultured and solid-cultured fungus bodies that, in the case when a biofilm is formed by culturing NBRC3740 strain on a solid culture medium, the biofilm has an ability to inhibit disease damage on a plant, which is very weak but not a little.

Example 9

In this Example, an experiment for inhibiting the proliferation of a plant pathogenic bacterium *Rhizoctonia* solani was conducted by using *Collimonas fungivorans* DMZ17622 strain, which is another *Collimonas* bacterium.

The D-25 strain and *Collimonas fungivorans* DMZ17622 strain were each applied in a reticular pattern onto a 1/10 TSA culture medium. Thereafter, a plant pathogenic bacterium *Rhizoctonia solani* was seeded to the center of each culture medium, and the abilities to inhibit the proliferation of the plant pathogenic bacterium were compared.

Figure 18:
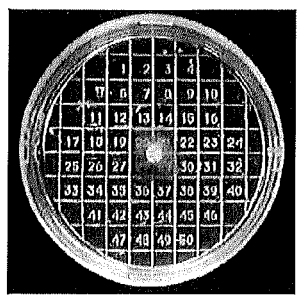
FIG. 18(*a*) is an observation drawing of the inhibition of the proliferation of *Rhizoctonia solani* by D-25 strain cultured on a 1/10 TSA culture medium on the 1$^{st}$ day, FIG. 18 (*b*) is an observation drawing on the 3$^{rd}$ day in the same case, FIG. 18 (*c*) is an observation drawing on the 7$^{th}$ day in the same case, FIG. 18(*d*) is an observation drawing of the inhibition of the proliferation of *Rhizoctonia solani* by DMZ17622 strain cultured on a 1/10 TSA culture medium on the 1$^{st}$ day, FIG. 18(*e*) is an observation drawing on the 3$^{rd}$ day in the same case, and FIG. 18(*f*) is an observation drawing on the 7$^{th}$ day in the same case.
Figure 18:
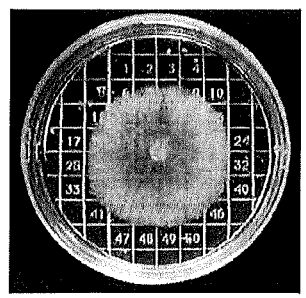
Figure 18:
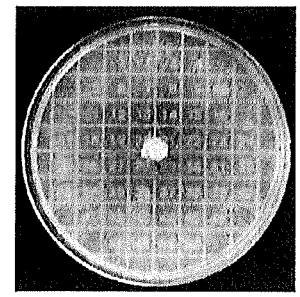
Figure 18:
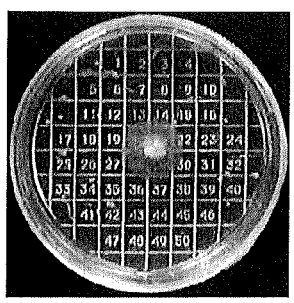
Figure 18:
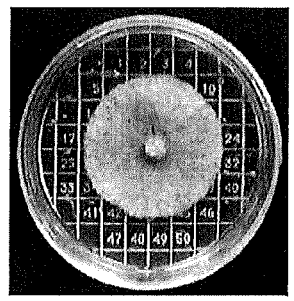
Figure 18:
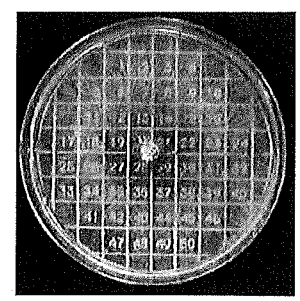

As shown in FIG. 18, no difference in the strengths of the inhibition of the proliferation of the plant pathogenic bacterium *Rhizoctonia solani* was observed in either of the two kinds of *Collimonas* bacteria, and either of the bacteria did not inhibit the proliferation of the plant pathogenic bacterium *Rhizoctonia solani*. In other words, in a low nutrient condition under which the D-25 strain cannot inhibit such as a 1/10 TSA culture medium, *Collimonas fungivorans* either did not show an ability to inhibit proliferation.

Therefore, the culture medium for culturing was changed to a TSA culture medium, and the abilities of the D-25 strain and *Collimonas fungivorans* DMZ17622 strain to inhibit a plant pathogenic bacterium were compared.

The D-25 strain and *Collimonas fungivorans* DMZ17622 strain were each applied onto a TSA culture medium in square shapes so as to doubly surround the culture medium, a plant pathogenic bacterium *Rhizoctonia solani* was seeded to the center of the above-mentioned culture medium and cultured at 25° C., and the abilities of the above-mentioned two strains to inhibit the proliferation of the plant pathogenic bacterium *Rhizoctonia solani* were compared.

Figure 19:
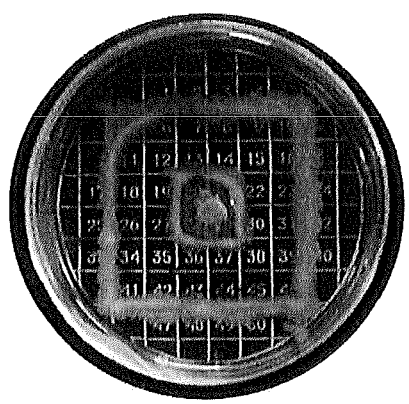
FIG. 19(*a*) is an observation drawing of the inhibition of the proliferation of *Rhizoctonia solani* by D-25 strain cultured on a TSA culture medium, and FIG. 19(*b*) is an observation drawing of the inhibition of the proliferation of *Rhizoctonia solani* by DMZ17622 strain cultured on a TSA culture medium.
Figure 19:
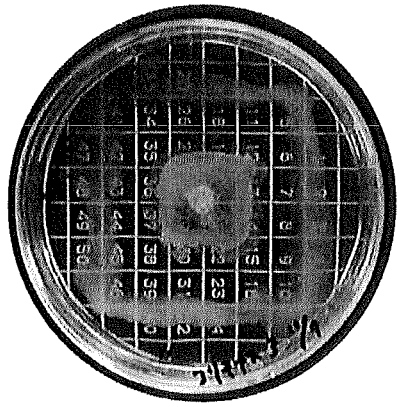

FIG. 19 is a photograph on the $4^{th}$ day of the culturing, and the abilities of the above-mentioned two strains to inhibit the proliferation of the plant pathogenic bacterium *Rhizoctonia solani* were equal, and the plant pathogenic bacterium *Rhizoctonia solani* was enclosed in the square of the center part in both culture media. However, it was observed that the proliferation speed was faster and the adhesion force was stronger in the *Collimonas fungivorans* DMZ17622 strain than those of the D-25 strain.

It was confirmed from the experimental results of the present Example and Example 8 that there is a difference in the abilities of *Collimonas* bacteria to inhibit the proliferation of a plant pathogenic bacterium depending on species, but the ability newly appears by culturing a solid biofilm.

(Conclusion)

As shown in Example 7, it was confirmed that the inhibition of the proliferation of a plant pathogenic bacterium by a *Collimonas* bacterium is different from an ability of inhibiting disease damage on a plant by the formation of an antibiotic substance, which is generally used in bioagrochemicals, as in *Bacillus* bacteria and the like.

Furthermore, in Example 9, *Collimonas fungivorans* DMZ17622 strain was subjected to the test, and it has been proved that this bacterial species depends on the mycophagous action of chitinase that has been known (Non-Patent Literature 7). It was strongly suggested by these experimental results that the main activity mechanism of the ability of a *Collimonas* bacterium to inhibit the proliferation of a plant pathogenic bacterium is chitinase generated by a fungus body.

It was confirmed that the three fungus bodies used in the exemplary embodiments of the present invention (D-25 strain, NBRC3740 strain and DMZ17622 strain) do not show a significant inhibition activity on oligotrophic culture media such as 1/10 TSB that have been subjected to the previous experiments, but it was confirmed that the hidden preventive abilities thereof significantly appear by providing the fungus bodies with not a vegetative cell state by aerated and agitated culturing or the like, which is generally used in the culturing of a bacterium, but culturing of a solid biofilm in which a nutrient source is ordinarily present. Furthermore, it can safely be said that, although there is a difference in the abilities of *Collimonas* bacteria to inhibit the proliferation of a plant pathogenic bacterium, all *Collimonas* bacteria inherently have not a little ability.

In addition, as described in Non-Patent Literature 8, some of extracellular polysaccharides, which are the main compositions of a biofilm formed by a bacterium, have antibacterial activities. Therefore, the abilities can also be considered to be synergistic effects by the chitinase of the *Collimonas* bacteria and extracellular polysaccharides.

In Non-Patent Literature 9, it is shown that, in the case when a *Collimonas* bacterium encounters a plant pathogenic bacterium under an oligotrophic condition, and in the case when the *Collimonas* bacterium is in an excessively stressed state, the *Collimonas* bacterium is put into a slime-like form (it is suggested that this means a biofilm) to express an antibacterial activity. Furthermore, this document suggests a possibility that the same phenomenon occurs also in a *Collimonas* bacterium, with citing that a *Xanthomonas* bacterium is put into a slime-like form so as to dissipate an excessive carbon source, due to the stress and growth-arrested state by an acid. However, Non-Patent Literature 9 tested *Collimonas fungivorans* Ter331 strain, which is a strain that allows the appearance of an ability to inhibit the proliferation of a plant pathogenic bacterium even in an oligotrophic environment such as 1/10 TSB, and finally concluded that a gene that controls the mycophagous ability of a *Collimonas* bacterium is expressed under an oligotrophic environment.

On the other hand, the present invention has succeeded in causing the appearance of the ability of a fungus body by forming the fungus body into a biofilm by enrichment even when the fungus body is a fungus body that does not cause the appearance of an ability to inhibit the proliferation of a plant pathogenic bacterium, which is significant in an oligotrophic environment.

In the case of a *Xanthomonas* bacterium, it is suggested that the bacterium is formed into a slime-like form so as to dissipate an excessive carbon source, due to the growth arrest by the stress by an acid, and the like, whereas in the present invention, a slime-like colony that actively grows of a *Collimonas* bacterium is sufficiently grown in an enriched environment from the initial stage of culturing, and thereafter a method of causing the appearance of an ability of inhibiting the proliferation of a plant pathogenic bacterium is provided.

Therefore, it can be judged that, in the expression of the ability of a *Collimonas* bacterium to inhibit the proliferation of a plant pathogenic bacterium, the mycophagous ability that is inherently possessed by the bacterium is expressed or amplified by culturing a slime-like biofilm, but it is not necessarily an absolute requirement that the bacterium is exposed to oligotrophy, but it is rather effective for this bacterium to prevent a plant pathogenic bacterium to provide the expression of a slime-like biofilm under an environment of a solid culture medium in which nutrient components are ordinarily present and an excess water content is absent.

Furthermore, as shown in the above-mentioned experiment of "Change in number of bacteria of *Collimonas* bacterium in sterilized soil", in the case when a *Collimonas* bacterium, even if it is a colony formed by a different culturing environment from the natural world, is put into a foreign soil, it maintains equivalent survivability to those of the number of bacteria that generally occur in the natural world, even when the inside of the soil is an oligotrophic environment. Therefore, the stability of the expression of the effect of inhibiting the proliferation of a plant pathogenic bacterium can be expected.

The preferable exemplary embodiments of the present invention have been explained above with referring to the attached drawings, but the present invention is not limited to such exemplary embodiments, and can be modified into various forms within a technical scope that is understood from the description of the claims.

For example, it is considered that strains belonging to the genus *Collimonas* other than the D-25 strain, NBRC3740 strain and DMZ 17622 strain can also exert an effect of inhibiting the proliferation of the plant pathogenic bacteria that are shown in the above-mentioned exemplary embodiments, *Rhizoctonia solani* and *Fusarium oxysporum*.

The invention claimed is:

1. A method of inhibiting the growth of a plant-pathogenic fungus, comprising the step of applying to the soil or to the water in which a plant that can be infected by the fungus grows an effective amount of the bacterium *Collimonas*, accession no. NITE P-1104.

2. The method of claim 1, wherein the plant-pathogenic fungus is of the genus *Rhizoctonia*.

3. The method of claim 1, wherein the plant-pathogenic fungus is of the genus *Fusarium*.

4. The method of claim 1, wherein the *Collimonas*, accession no. NITE P-1104, before being applied to soil or water, was cultured on a culture medium in which the culture medium components were not diluted.

5. The method of claim 4, wherein the *Collimonas*, accession no. NITE P-1104, forms a biofilm on the culture medium.

* * * * *